(12) United States Patent
Piontkowski

(10) Patent No.: US 7,420,731 B2
(45) Date of Patent: *Sep. 2, 2008

(54) SURGICAL MICROSCOPE SUPPORT SYSTEM

(76) Inventor: Paul K. Piontkowski, 2310 Popkins La., Alexandria, VA (US) 22306

( * ) Notice: Subject to any disclaimer, the term of this patent is extended or adjusted under 35 U.S.C. 154(b) by 25 days.

This patent is subject to a terminal disclaimer.

(21) Appl. No.: 11/088,229

(22) Filed: Mar. 23, 2005

(65) Prior Publication Data

US 2006/0126167 A1 Jun. 15, 2006

Related U.S. Application Data

(60) Provisional application No. 60/635,625, filed on Dec. 14, 2004.

(51) Int. Cl.
G02B 21/00 (2006.01)
(52) U.S. Cl. .................. 359/382; 359/368; 248/123.11
(58) Field of Classification Search ................. 359/382, 359/368; 248/123.11, 123.2
See application file for complete search history.

(56) References Cited

U.S. PATENT DOCUMENTS

| 3,090,045 | A | | 5/1963 | Hurst |
| 3,290,985 | A | * | 12/1966 | Bains et al. ................. 359/896 |
| 3,434,772 | A | | 3/1969 | Fogle |
| 3,796,220 | A | | 3/1974 | Bredemeier |
| 3,830,230 | A | | 8/1974 | Chester |
| 4,170,336 | A | | 10/1979 | Malis |
| 4,175,826 | A | | 11/1979 | Blaha et al. |
| 4,344,595 | A | | 8/1982 | Heller et al. |
| 4,364,629 | A | | 12/1982 | Lang et al. |
| 4,396,260 | A | | 8/1983 | Takizawa et al. |
| 4,515,333 | A | | 5/1985 | Pugh et al. |
| 4,518,231 | A | | 5/1985 | Muchel et al. |
| 4,594,608 | A | | 6/1986 | Hatae et al. |
| 4,614,411 | A | | 9/1986 | Horenz |
| 4,616,257 | A | * | 10/1986 | Kloots et al. ................. 348/370 |
| 4,657,356 | A | | 4/1987 | Matsumura |
| 4,787,734 | A | | 11/1988 | Matsumura |
| 4,849,778 | A | | 7/1989 | Samuelson |
| 4,895,328 | A | * | 1/1990 | Ryan ....................... 248/124.1 |

(Continued)

FOREIGN PATENT DOCUMENTS

WO 9203756 5/1992

(Continued)

OTHER PUBLICATIONS

Prior Art—Advertisement—Varioscope M5 by Life Optics, Sep. 24, 2004.

(Continued)

Primary Examiner—Lee Fineman
(74) Attorney, Agent, or Firm—Dority & Manning, P.A.

(57) ABSTRACT

A microscope system includes an adjustable arm attached at one end to a support mount. A suspension member is configured at an opposite end of the adjustable arm and supports a scope assembly. The scope assembly includes a head harness and a microscope adjustably connected to the harness such that the microscope is disposed along an operator's line of site upon the operator donning the head harness. A weight compensator device is configured on the arm to compensate for the weight of the scope assembly hanging on the suspension member.

27 Claims, 6 Drawing Sheets

U.S. PATENT DOCUMENTS

| | | | |
|---|---|---|---|
| 5,213,293 A | 5/1993 | Muentener et al. | |
| 5,252,070 A | 10/1993 | Jarrett | |
| 5,253,832 A | 10/1993 | Bolas et al. | |
| 5,257,998 A | 11/1993 | Ota et al. | |
| 5,345,087 A * | 9/1994 | Luber et al. | 250/559.29 |
| 5,365,607 A | 11/1994 | Benevento, Jr. et al. | |
| 5,420,716 A | 5/1995 | Fukaya | |
| 5,537,248 A | 7/1996 | Sander | |
| 5,642,220 A | 6/1997 | Kleinberg et al. | |
| 5,667,186 A | 9/1997 | Luber | |
| 5,748,366 A | 5/1998 | Yasunaga et al. | |
| 5,841,509 A | 11/1998 | Harooni et al. | |
| 5,913,412 A | 6/1999 | Huber et al. | |
| 6,081,372 A | 6/2000 | Mura | |
| 6,147,800 A | 11/2000 | Faber | |
| 6,290,368 B1 * | 9/2001 | Lehrer | 362/187 |
| 6,334,595 B1 * | 1/2002 | Stenkvist et al. | 248/125.2 |
| 6,471,165 B2 * | 10/2002 | Twisselmann | 248/123.11 |
| 6,543,914 B2 | 4/2003 | Sander | |
| 6,606,192 B2 * | 8/2003 | Haran | 359/409 |
| 6,763,286 B2 * | 7/2004 | Metelski | 700/279 |
| 6,859,312 B1 * | 2/2005 | Atchison | 359/380 |

FOREIGN PATENT DOCUMENTS

| | | |
|---|---|---|
| WO | 9609566 | 3/1996 |
| WO | 0055673 A1 | 9/2000 |
| WO | 0138919 A1 | 5/2001 |
| WO | 03069214 | 8/2003 |

OTHER PUBLICATIONS

Prior Art—Advertisement—Varioscope AF3 by Life Optics, Sep. 24, 2004.

Prior Art—Advertisement—Seiler Instrument Microscope Division—Model SSI-202 Dental Microscope, Sep. 24, 2004.

* cited by examiner

SURGICAL MICROSCOPE SUPPORT SYSTEM

PRIORITY CLAIM

The present application claims priority to U.S. Provisional Patent Application No. 60/635,625 filed on Dec. 14, 2004.

RELATED APPLICATIONS

The present application is related in subject matter to the co-pending U.S. application Ser. Nos. 10/320,385 filed on Dec. 17, 2002, and Ser. No. 10/646,929 filed on Aug. 25, 2003, from the same inventor. The '385 and '929 applications are incorporated herein in their entirety for all purposes.

FIELD OF THE INVENTION

The present invention relates to the field of binocular microscope systems used, for example, in various surgical procedures, and more particularly to an improved support system for a binocular microscope.

BACKGROUND

The need for magnification of a surgical or medical procedure site is widely recognized in the medical arts, and a number of devices are available for this purpose. The most common device is the loupe (or pair of loupes), which is essentially a lens mounted to an eyeglass frame. Although the loupe is relatively inexpensive and suffices for certain procedures, the magnification factor of the device is limited and the loupe is inadequate for a wide range of procedures.

Recognizing the need for increased magnification, the art turned to various types of surgical microscope configurations. One such device is a self-contained head mounted system wherein the microscope and associated components are mounted on a head harness worn by the surgeon. Reference is made, for example, to the devices described in U.S. Pat. No. 4,616,257 and the PCT application WO 03/069214. More recently, the company Life Optics Corporation having a principal place of business in Chicago, Ill., has introduced a line of head-mounted microscopes under the family name "Varioscope®" for use in surgical and dental procedures.

A drawback, however, with the head mounted systems is that the overall weight of the system is borne essentially entirely by the operator's head. This can be problematic, particularly during relatively long and intense procedures wherein any variable that adds to surgeon fatigue should be minimized. The head mounted systems may even include counterweights at the back of the head harness to offset the weight of the scope at the front of the harness. These counterweights only add to the overall weight of the device. The effort to overcome the inertia of the relatively heavy head mounted systems, and subsequent braking of the motion of the system at a desired position and angular orientation of the scope, is an unnatural exercise for the surgeon and can make the device difficult and frustrating to use. This is particularly true at higher magnification powers wherein even a slight positional overshoot of the scope may result in a total loss of the relevant viewing field and a subsequent erratic "hunt-and-seek" effort to relocate the viewing field.

Analytical microscope systems are also known wherein the scope is supported by an adjustable structure, such as an articulated, counterbalanced boom-type structure. Reference is made, for example, to the devices described in U.S. Pat. Nos. 4,344,595; 4,515,333; and 5,253,832. Seiler Instrument & Manufacturing Company of St. Louis, Mo., manufactures and markets a line of dental microscopes (Model SSI) with a binocular scope on a counterbalanced pantographic arm. The optical head is manually positioned with handles provided on the head unit, and the scope is focused either manually or by a foot controlled motorized unit. In general, these devices utilize various mechanical configurations to support the scope at a fully supported position and angular orientation. In this regard, such systems may be considered as externally stabilized systems wherein the position of the scope is manually adjusted and then maintained by the support structure independent of the position of the operator's head. In other words, orientation of the operator's line of sight (and thus the visual field) is dictated by the static position of the externally supported scope. The scope does not follow movement of the operator's head. Certain of these externally stabilized systems may utilize a power assist drive unit, such as an electrical or hydraulic motor, to position the scope and relatively heavy support structure.

An inherent drawback of the externally stabilized suspended systems is that the procedure must be stopped in order to reposition the scope, particularly if this must be done by hand with handles provided on the optical heads. Additionally, upon repositioning the scope, the overall weight of the scope and support structure results in a momentum that tends to carry the device beyond its desired position, often resulting in numerous and embarrassing attempts to correctly position the scope. The power assist devices offer some improvement in this area, but are complicated, cost prohibitive for many practitioners, and do not offer total uninhibited range and motion of the scope. They also require a high degree of spatial coordination by the operator to externally drive the optical head with a power unit to a desired orientation while looking through the scope. Again, position of the scope is not slaved to movement of the operator's head, but to external manual or power manipulation of the optical head unit.

A need therefore exists for an improved system and apparatus for supporting a surgical microscope that is lightweight, easy to use, relatively uncomplicated and affordable, and addresses drawbacks of the known systems. The present invention provides such a system.

SUMMARY

Various features and advantages of the invention will be set forth in the following description, or may be obvious from the description, or may be learned from practice of the invention.

The present invention provides a support system for a microscope that provides generally uninhibited total freedom of movement for the operator. The scope is aligned with the operator's line of sight and is slaved to movement of the operator's head with minimum force required to position or manipulate the scope. In this way, use of the scope is essentially a natural extension the operator's eyes, and the operator is far less likely to loose the relevant field of view, even with maximum magnification.

The invention is premised on providing an inherently unstable support for the scope such that the scope is essentially free-floating and subject to movement from any manner of relatively little external force. The scope is not stabilized until a head harness attached to the scope is donned by an operator. It is the operator that stabilizes the suspended scope at a desired position and orientation, not the support structure.

In a particular embodiment, the microscope support system includes an adjustable arm attached at one end to a support mount. The arm may be configured from any number of individual arm segments that are pivotally connected so as to be adjustable in a horizontal plane, a vertical plane, or both planes. The support mount may be any manner of ceiling mount, wall mount, floor mount, portable movable mount, and so forth. The arm may be adjustable relative to the respective mount. The arm and support mount configuration may be widely varied to provide a broad coverage "range" for the system from a permanent or portable installation site within a treatment room.

A suspension member is configured proximal to an opposite end of the adjustable arm. It should be appreciated that the suspension member may be any manner of device that allows for generally universal movement of a scope assembly supported by the suspension member, as described below. For example, the suspension member may be a chain or series of relatively rigid articulated members, or a single member articulated at its opposite ends by any manner of conventional joint. In a particular embodiment, the suspension member may be any length of flexible or pliable material "cable" material, such as a cord or rope-like member, or other material that is readily foldable upon itself. It this regard, it should be understood that the term "cable" is used in a generic sense to encompass any manner of flexible or pliable member such as wire, cord, rope, chain, straps, and so forth. The suspension member may be attached to the adjustable arm by any conventional means, including a quick disconnect device, swivel device, and so forth.

A scope assembly is connected to the opposite end of the suspension member so as to hang from the suspension member. The scope assembly includes a head harness and a microscope adjustably connected to the harness so as to be oriented along the operator's line of sight upon the operator donning the head harness. It should be appreciated that the present invention is not limited to any particular type of microscope. In a desirable embodiment, the scope is a binocular microscope. Any number of commercially available scopes may be configured for use with the present support system, or a custom scope may be designed specifically for use with the support system. A suitable scope is described, for example, in co-pending U.S. patent application Ser. No. 10/646,929 from the same inventor filed on Aug. 25, 2003, which is incorporated herein in its entirety for all purposes.

An adjustable weight compensator device is configured relative to the adjustable arm to counterbalance the weight of the scope assembly hanging on the suspension member. The weight compensator is adjustable such that, depending on the overall weight of the scope assembly, the system is adjusted so that the scope assembly assumes an essentially "free-floating" posture prior to the operator donning the head harness. In this free-floating state, the hanging scope assembly may be moved in virtually any direction with minimal force, including a vertical direction. Movement in a horizontal plane is virtually uninhibited due to the pliable nature of the suspension member. For upwards vertical movement, the weight compensator immediately "absorbs" any slack in the suspension member such that the weight of the scope assembly is borne by the adjustable arm, and not the operator. With this configuration, once the head harness is properly donned by the operator, the scope becomes a natural extension along the operator's line of sight and the position and angular orientation of the scope is slaved to movement of the operator's head with minimal force required by the operator to move an maintain position of the scope.

Desirably, the amount of force required by the operator to move the scope assembly in any direction is barely perceptible, and in a particular embodiment is generally less than about 2.5 lbs of force to move the scope assembly in any direction from its initial free-floating state. In a particular embodiment, the amount of force is generally less than about 1.5 lbs, or about 1.0 lbs. The force (and capacity of the weight compensator) will also be a function of the overall weight of the scope assembly, and it may be desirable to minimize such weight. In one embodiment, the overall hanging weight of the scope assembly is generally less than about 8 lbs., and may be less than about 5 lbs.

The weight compensator may take on various configurations. In one embodiment, the weight compensator may be a spring mechanism connected between segments of the adjustable arm. For example, the suspension member may hang the scope assembly from the last of the arm segments, with such arm being vertically adjustable relative to its adjacent arm segment (which may be vertically fixed). The spring mechanism can be operably connected between the vertically fixed and vertically adjustable arm segments such that the weight of the scope assembly tending to pull the vertically adjustable arm downward is compensated for by the spring mechanism. The spring mechanism is preferably adjustable so that the support system may be used with scope assemblies of varying weight. The spring mechanism may be any conventional spring device, such as a gas spring, a coil spring, and so forth.

In an alternate embodiment wherein the suspension member is a cable member, the weight compensator may be an adjustable line tensioner device configured with the cable suspension member to take up slack in the suspension member or pay out additional length of the suspension member as the operator repositions the scope assembly. Such tensioner devices are well known and typically include a reel and spring that is "wound" or tightened as additional weight is added to the device. Any number of commercially available tensioner devices may be configured and modified as needed for use with the present invention.

Desirably, relevant movement between the operator's head and the scope assembly should be eliminated as much as possible. The scope should move and stop precisely with respective movement and stopping of the operator's head. In this way, the scope is always oriented along the operator's line of sight. The scope assembly plays an important role in this regard. The head harness must ensure that relative movement between the operator's head and the harness is prevented. Similarly, the mounting connection between the scope and the head harness should prevent relative movement between the two components. In a particular embodiment, the head harness comprises one or more adjustable strap members that encircle the operator's head. An additional strap member may be provided that passes over the operator's head. The strap configuration should be comfortable for the operator over an extended period of time while ensuring a tight and secure fit of the scope assembly to the operator's head. Any manner of adjustable mechanism, such as a buckle, hook and loop material, tightening knob, and so forth, may be used to tighten or loosen the straps on the operator's head.

It should be appreciated that the head harness is not limited to a strap configuration, but may also include a helmet-like structure or other head covering structure, whether flexible or rigid.

The scope assembly may include a rigid mounting fixture configured on the head harness, the scope being attached to the mounting fixture. One particular embodiment of a mounting fixture includes a rigid material band coincident with the strap member around at least a portion of the operator's head, and a mounting plate attached to the rigid material band in the area of the operator's forehead. The scope may be attached to the mounting plate via a rigid connecting arm, the connecting arm in turn being adjustable relative to the mounting plate. The scope may also be adjustable in position relative to the connecting arm.

Aspects of the invention will be described in greater detail below through reference to the embodiments illustrated in the attached drawings.

DETAILED DESCRIPTION

Figure 1:
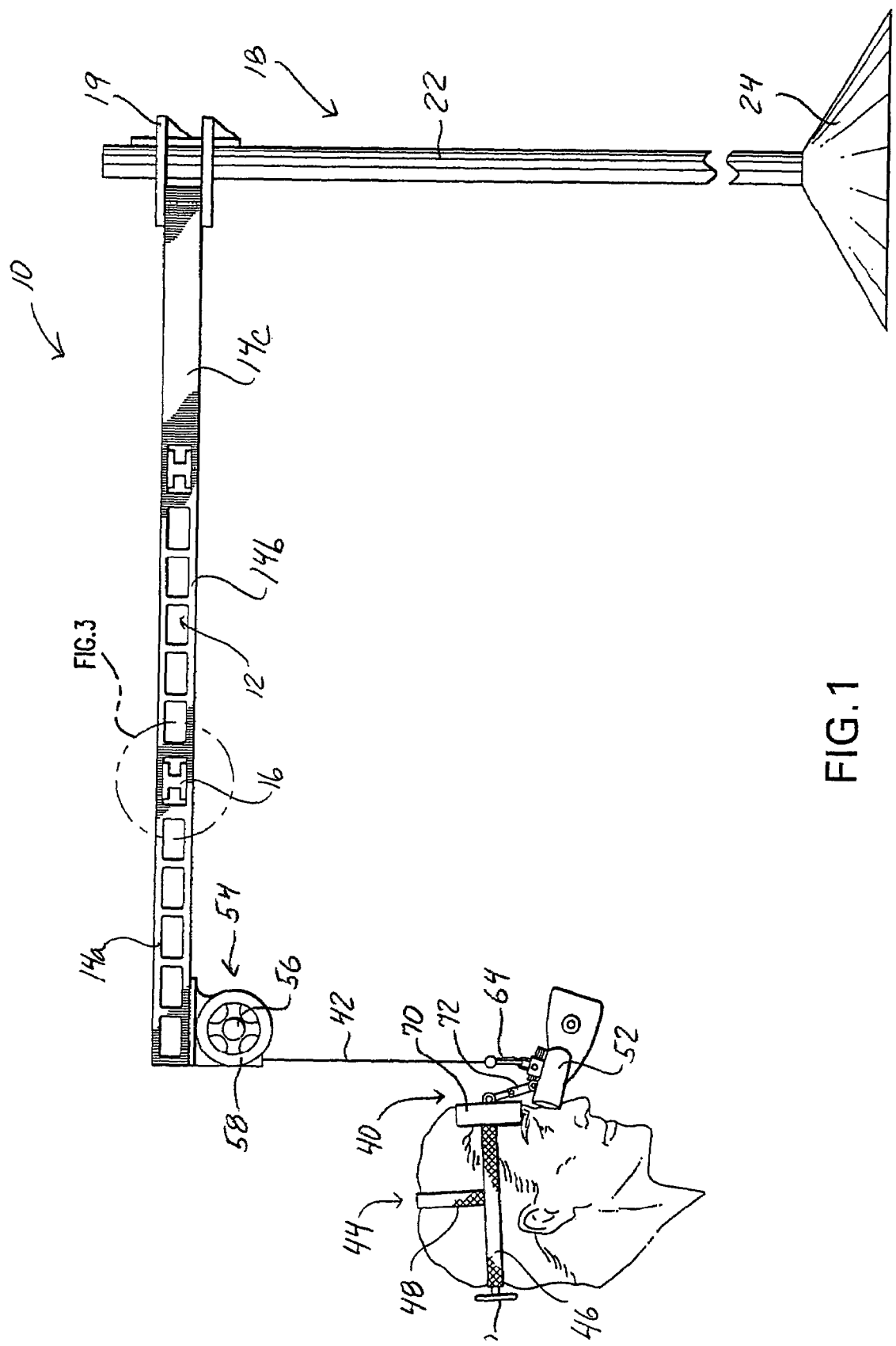
FIG. 1 is a perspective side view of an embodiment of a microscope system according to the invention.

Reference will now be made in detail to one or more embodiments of the invention, examples of which are graphically illustrated in the drawings. The embodiments are provided by way of explanation of the invention, and not meant as a limitation of the invention. For example, features illustrated or described as part of one embodiment may be utilized with another embodiment to yield still a further embodiment. It is intended that the present invention include these and other modifications and variations.

Various embodiments of a microscope system 10 according to the invention are illustrated in the figures. In the embodiment of FIG. 1, the microscope system 10 includes an adjustable arm 12 attached to a support mount 18. The mount 18 may take on various configurations. In the illustrated embodiment, mount 18 includes a vertically extending support pole 22 attached to a base unit 24. The base unit 24 may be stationary, wheeled, etc. Additionally, the support pole 22 may be adjustable in height relative to the base unit 24. The adjustable arm 12 is connected to the support mount 18 via a connection member 19. This member 19 may be a hinge or other type of pivotal connector that allows the arm 12 to rotate relative to the vertical support pole 22.

The adjustable arm 12 may be configured from any number of individual arm segments 14a, 14b, 14c that are pivotally connected to each other via a coupling member 16 such that the individual arm segments 14a, 14b, 14c are adjustable in one or both of a horizontal plane or vertical plane relative to each other. In the embodiment of FIG. 1, the individual arm segments are adjustable in a horizontal plane. Any manner of conventional swivel or pivoting type connection may be made between the individual arm segments 14a, 14b, and 14c.

Figure 3:
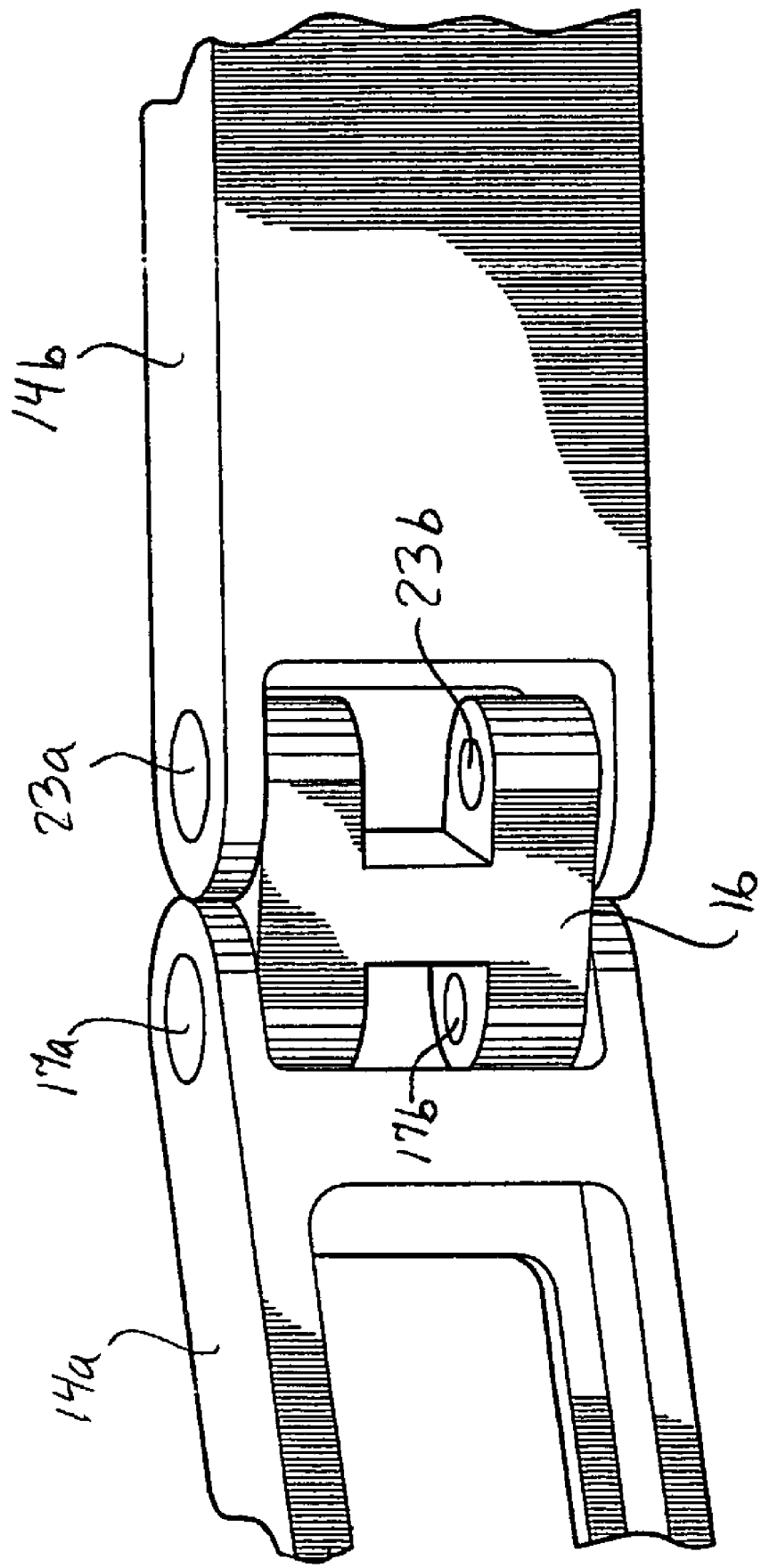
FIG. 3 is a perspective view of a pivotal coupling between the arm segments of the embodiment of FIG. 1.

The coupling member 16 used in the embodiment of FIG. 1 is illustrated in greater detail in FIG. 3. The coupling member 16 is an intermediary member between the individual arm segments 14a, 14b and is hinged to the ends of the arm segments via pins 17a, 17b, 23a, and 23b. It should also be appreciated that the arms 14a and 14b could readily be attached directly to each other through a single pin that defines a pivot axis for the arms. The invention is not limited to any particular type of connection between the individual arm segments.

Referring again to FIG. 1, a suspension member 42 is connected generally at or near the end of the outermost arm segment 14a. In this particular embodiment, the suspension member 42 is a wire or cable member, but, as mentioned, may be any flexible or pliable material that functions as a cord or rope-like member in that it is pliant and foldable upon itself. Alternatively, the suspension member 42 may be a chain or articulated rigid members, links, or segments, or a single rigid segment articulated at both ends by, for example, universal joints or couplings. For the present description, the suspension member 42 is illustrated and described as a cable suspension member as illustrative of a suitable embodiment.

The suspension member 42 may include a quick disconnect device 64 at one or both ends thereof for attachment to the adjustable arm 12 at one end and/or to a scope assembly 40 at the opposite end, as described in greater detail below. The quick disconnect device 64 may be, for example, a hook, clasp, or any other well known disconnect device.

A scope assembly 40 is connected so as to essentially hang from the suspension member 42. As mentioned, the scope assembly 40 may be connected to the suspension member 42 via a quick disconnect 64. The scope assembly 40 includes a head harness 44 and a microscope 52. The microscope 52 is adjustably connected to the head harness 44 so that the scope 52 can be oriented along the operator's line of sight upon the operator donning the head harness, as depicted in FIG. 1. The scope assembly 40 will be described in greater detail below with reference to FIGS. 5 and 6.

The microscope assembly 10 includes an adjustable weight compensator device, generally 54. The compensator device counterbalances the weight of the scope assembly 40 hanging on the suspension member 42. The compensator device 54 is adjustable so that, depending on the overall weight of the scope assembly 40, the scope assembly 40 assumes an essentially "free-floating" posture prior to the operator donning the head harness 44. In this posture, the scope assembly 40 is movable in virtually any direction with minimal force, including a vertical direction. In the embodiment illustrated in FIGS. 1 and 2, the weight compensator device 54 is a line tensioner device 56 that includes a spring loaded reel 58 around which the suspension member 42 runs. Various embodiments of the line tensioner device 56 are commercially available and may be utilized or modified for use with the microscope system 10 according to the invention. Embodiments of the line tensioner device 56 are known as "tool retractors", and are readily available at hardware stores, and the like. With use of such a device, the weight of the scope assembly 40 is borne by the adjustable arm 12, and any vertical movement of the scope assembly 40 relative to the arm 12 is compensated for by the line tensioner device 56.

Figure 4:
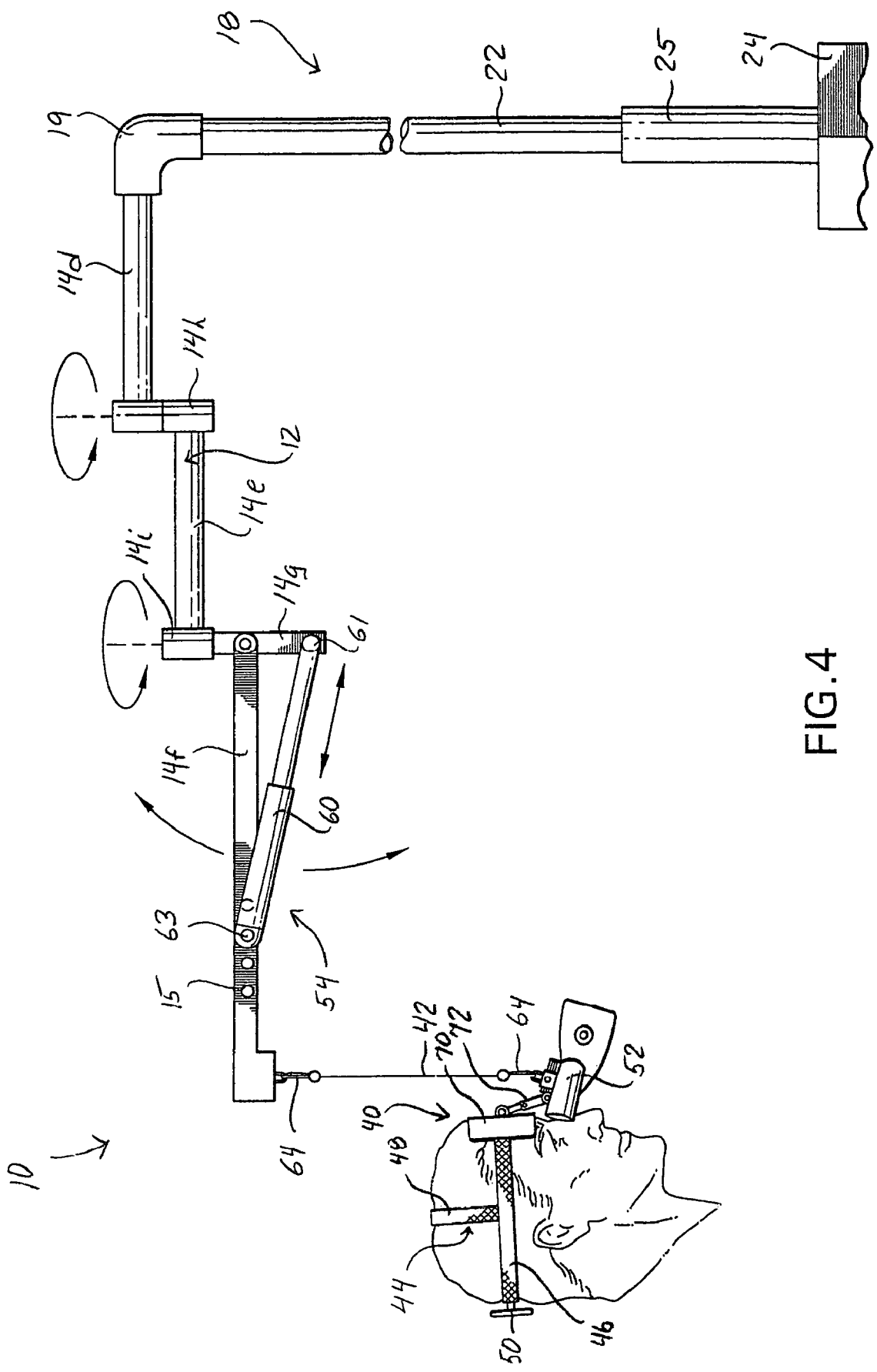
FIG. 4 is a perspective view of still another embodiment of a microscope system according to the invention.

In an alternate embodiment illustrated for example in FIG. 4, the weight compensator device 54 includes a spring mechanism 60 connected between adjacent segments 14f, 14e, of the adjustable arm 12. In this embodiment, the arm 12 includes arm segments 14d, 14e, and 14f. Arms 14e and 14d are pivotally connected to each other through a connector 14h. Likewise, arms 14e and 14f are pivotally connected relative to each other via a connector 14i. Arms 14d and 14e are adjustable in a horizontal plane relative to each other, but are otherwise vertically stable relative to each other. Arm 14d is connected via connector 19 to a support pole 22 that telescopes relative to member 25. The outermost arm 14f is pivotally connected to a vertical extension 14g so as to be vertically adjustable relative to the arm 14e, as depicted by the arrows in FIG. 4. The spring mechanism 60 is connected between arm 14f and the vertical extension 14g via pivotal connecting points 61, 63. The spring mechanism may be any manner of conventional spring device, such as a coil spring, gas spring, or the like. The spring mechanism 60 is adjustable in position relative to the arm 14f via the series of holes 15 defined in the arm 14f. The spring mechanism 60 has a preset or adjustable force to compensate for the weight of the scope assembly 40 suspended from the cable suspension member 42. Downward vertical movement of the scope assembly 40 results in the arm 14f pivoting downward against resistance of the spring mechanism 60. Upon the operator raising his head in a vertical direction, the spring mechanism 60 causes the arm 14f to rotate vertically upwards with the motion of the operator's head. The spring mechanism 60 is selected such that the amount of force necessary by the operator in order to move the scope assembly 40 in a downwards vertical direction, or to maintain the scope 40 stationary at a given vertical height is minimal.

With any embodiment of a weight compensator device 54, desirably the amount of force required by the operator to move the scope assembly 40 in any direction is barely perceptible, and preferably is generally less than about 2.5 lbs. of force to move the scope assembly 40 in any direction from its initial free floating state. Desirably, the amount of force may be less than about 1.5 lbs, or less than about 1.0 lbs. As mentioned, this force, and the design of the weight compensator 54 will be a function of the overall weight of the scope assembly 40 and anticipated range of motion necessary for the operator to carry out a given procedure while donning the scope assembly 40. In a particular embodiment, the overall hanging weight of the scope assembly 40 is generally less than about 8 lbs., and may be less than about 5 lbs.

The amount of force required to move the scope assembly in any direction may be measured with any conventional line tension measuring device or scale, such as a handheld scale similar to a recreational fish scale. The scale may be simply attached to the scope assembly 40 and used to pull the scope assembly 40 in any desired direction while recording the amount of force necessary to move the scope assembly 40.

Figure 2:
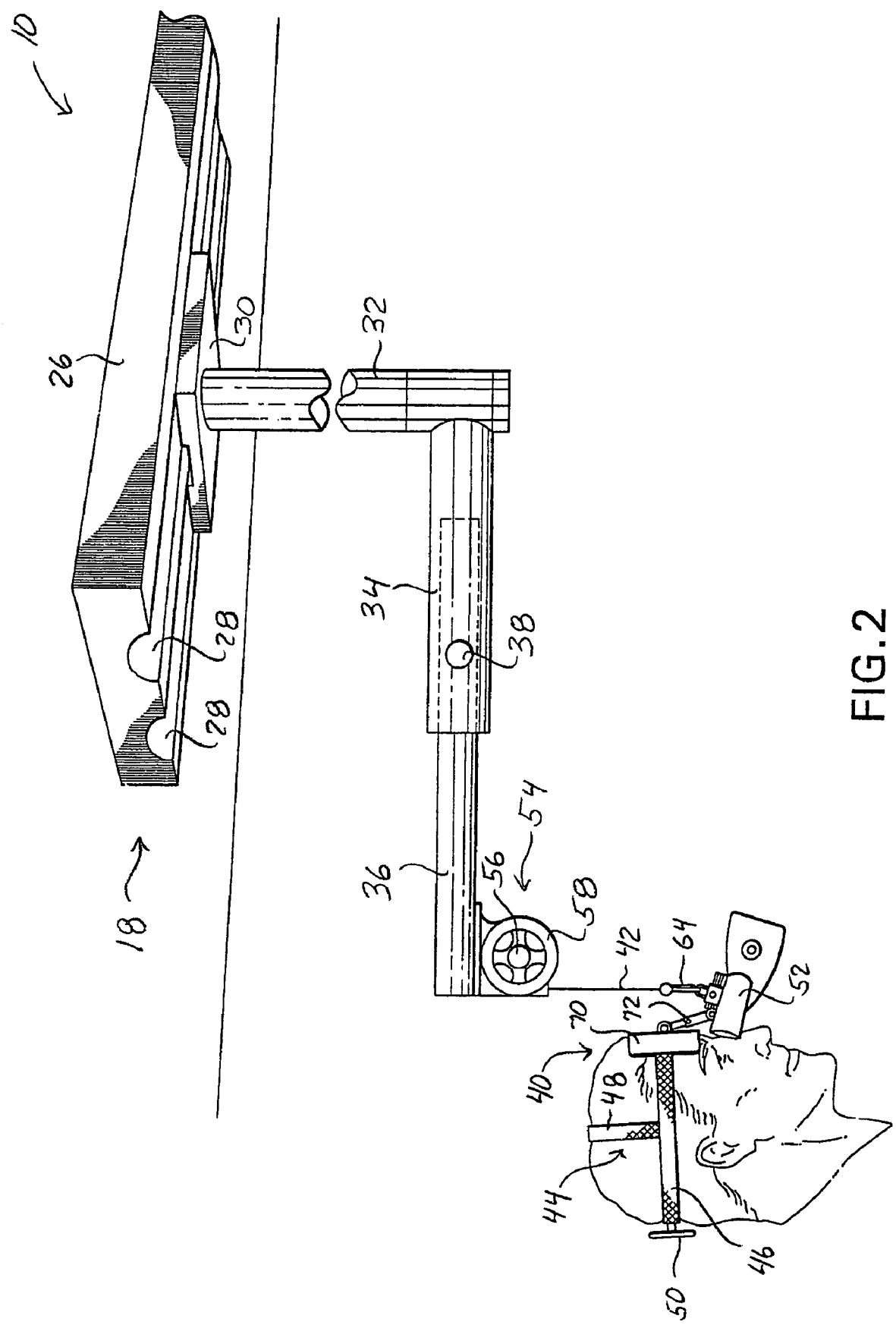
FIG. 2 is a perspective side view of an alternative embodiment of a microscope system according to the invention.

The embodiment of FIG. 2 illustrates a different support mount configuration 18 for the scope system 10. In this embodiment, the support mount 18 includes a ceiling support member 26 having tracks 28 defined therealong. A slide block 30 is adjustably positionable along the tracks 28. A vertical support 32 extends downwardly from the slide block 30. A first horizontal arm segment 34 extends from the vertical support 32, and a second horizontal arm segment 36 telescopes into the first arm segment 34. The overall horizontal length of the arm segments 36, 34 is adjusted by relative sliding between the arm segment 36 and arm segment 34, and may be locked via a locking pin 38.

It should be appreciated that any manner and configuration of support mounts 18 are within the scope and spirit of the invention for mounting the microscope system 10 to a floor, wall, ceiling, or other support structure.

Figure 5:
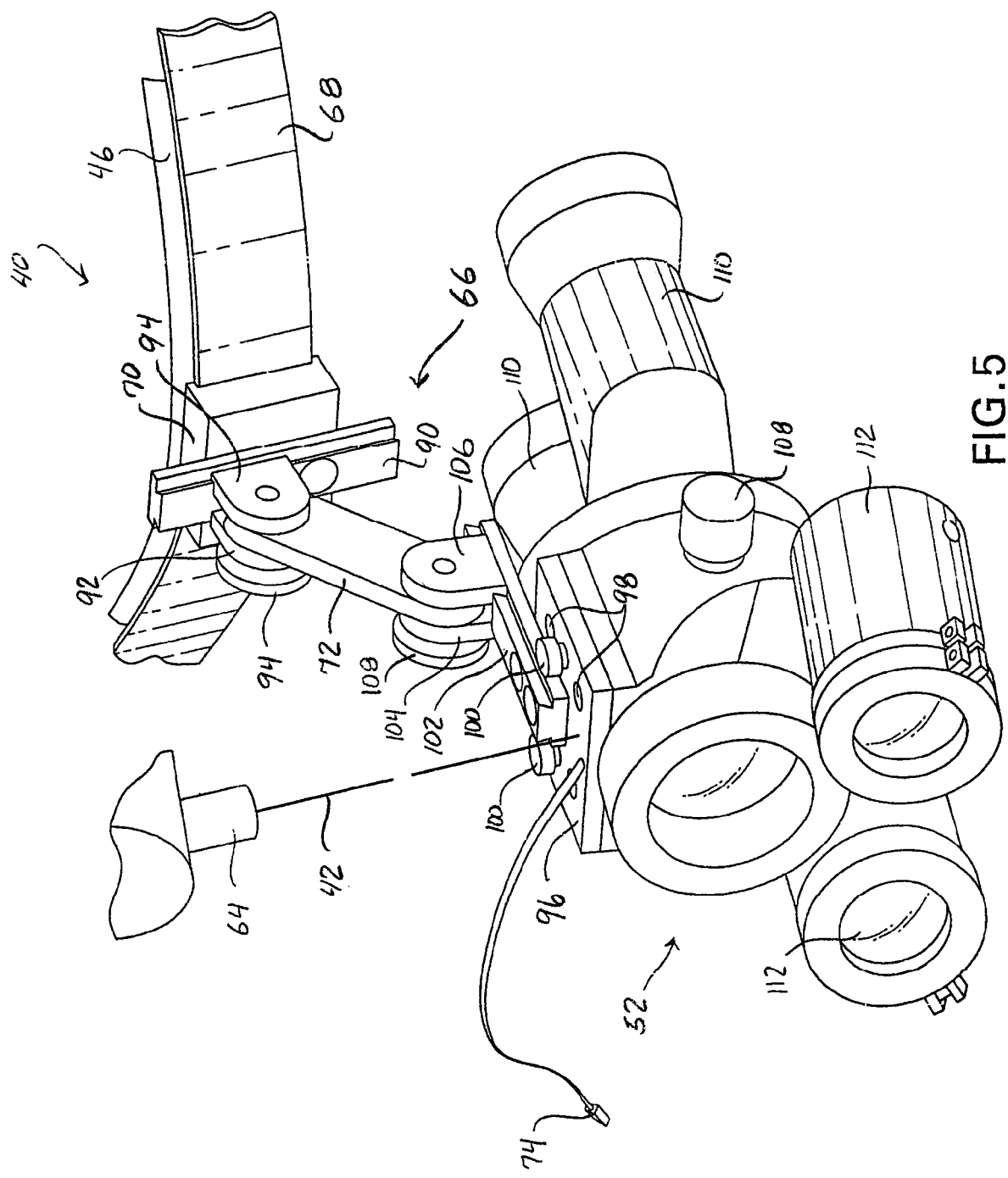
FIG. 5 is a perspective view of an embodiment of a suitable scope assembly that may be used in the microscope system.
Figure 6:
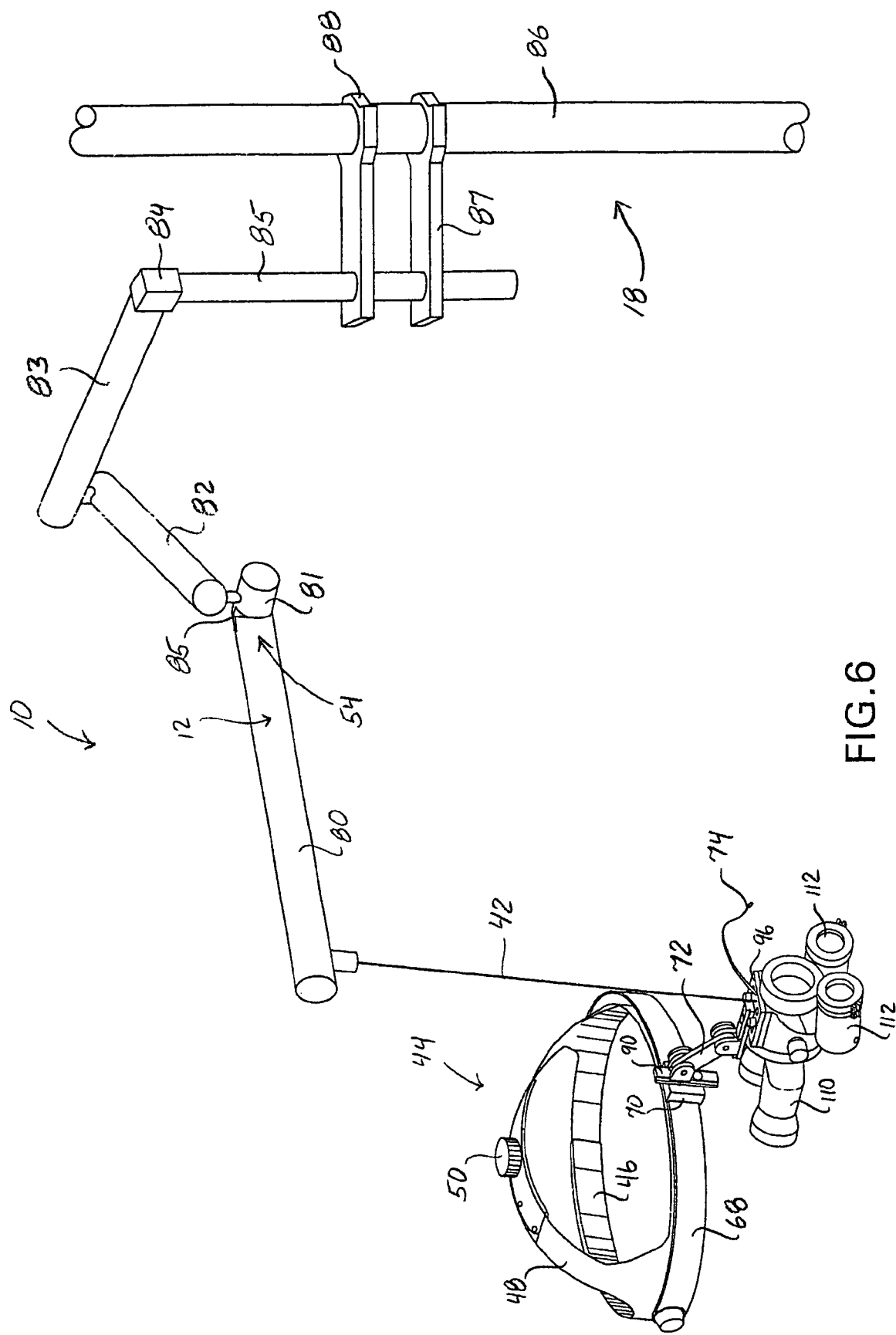
FIG. 6 is a perspective view of yet a different embodiment according to the invention.

As discussed, relative movement between the operator's head and the scope assembly 40 is undesirable. In this regard, the head harness 44 should ensure that relative movement between the operator's head and the head harness is minimized, as well as relative movement between the scope 52 and the head harness 44. An embodiment of a head harness 44 and system for mounting the scope 52 relative to the head harness 44 is illustrated in FIGS. 5 and 6. In this embodiment, the head harness 44 includes a first strap member 46 designed to generally encircle the operator's head. The strap 46 is adjustable by any conventional means, including a knob adjustment device 50 (FIGS. 1, 2, and 4), buckle, hook-and-loop material, and other conventional adjusting mechanism. The head harness 44 may include a second strap 48 that is designed to generally pass over the top of the operator's head as illustrated in FIGS. 1, 2, and 4. The second strap 48 may also be adjustable via a knob adjuster 50, or other suitable adjusting mechanism. The harness 44 should not be uncomfortable to the operator, yet must be capable of being securely fixed to the operator's head such that little or no vertical movement between the head harness 44 and the operator's head is experienced. Although illustrated as a strap configuration in the figures, it should be appreciated that the head harness 44 is not limited to such configuration, and may include a helmet-like structure or other head covering structure, whether flexible or rigid.

The scope assembly 40 includes a rigid mounting fixture 66 configured on the head harness 44, with the microscope 52 being attached to the mounting fixture 66 such that little or no relative movement exists between the scope 52 and head harness 44. An embodiment of a suitable mounting fixture 66 is illustrated in FIGS. 5 and 6.

Referring to FIGS. 5 and 6, the mounting fixture 66 includes a plate 70 connected to a rigid metal or plastic band 68. The band 68 is, in turn, connected to the first strap 46 of the head harness 44. The rigid band 68 has a length so as to encircle at least a part of the operator's head, for example from temple to temple. A vertically extending dovetail member 90 is attached to the plate 70. Mating dovetail joint portions 92, 94 clamp an adjustable connecting arm 72 by means of a screw 94 that extends through a hole in the dovetail joint portion 92, a hole in the arm 72, and into a screw threaded opening in the dovetail joint portion 94. A plate 96 is attached to an upper surface of a stereo binocular microscope 52 by means of screws 98. Screws 100 on opposite sides of the plate 96 are screw threaded into the plate 96 and abut against the upper surface of the microscope 52. By loosening screws 98 and adjusting the screws 100, the plate 96 can be tilted relative to the upper surface of the microscope 52 and used as a means for adjusting the microscope relative to the head and eyes of the operator.

An elongated dovetail 102 is connected to the plate 96, and a pair of mating dovetail joint portions 104, 106 are used to clamp the opposite end of the connecting arm 72 to the elongated dovetail 102 by means of a screw 108. It should thus be appreciated that the angular orientation of the microscope 52 and relative height of the scope with respect to the head harness 44 may also be adjusted by pivotal movement of the connecting arm 72 at either of its' ends.

It should also be appreciated that the embodiment of a suitable mounting fixture 66 illustrated in FIGS. 5 and 6 is exemplary only, and that any number of mechanical configurations may suffice as a suitable mounting fixture.

As discussed above, the microscope 52 is not limited to any particular make or type of scope, but is preferably a binocular stereo microscope as illustrated in the figures. Such scopes are readily available from any number of scope manufacturers. The scope illustrated in the figures includes a rotatable lens changer 108 and a pair of oculars 110. One or more LED light sources 112 having a selectable brightness are also provided and supplied with power via a power cord 74. The light sources 112 are positioned around the lens of the microscope 52 and are directed to the patient or object to be observed. The light sources 112 include lenses 113 to focus and direct the light towards the area in front of the microscope. A suitable microscope is described, for example, in co-pending U.S. patent application Ser. No. 10/646,929 filed on Aug. 25, 2003, which is incorporated herein in its entirety by reference for all purposes.

In the embodiment of FIG. 6, a different configuration of an adjustable arm 12 and support mount 18 are illustrated. In this embodiment, the support mount 18 includes a vertically extending support 86 that may extend, for example, between the floor and ceiling of a room, or be supported from the ceiling or in a floor base unit. Clamps 87 and 88 are provided to position a vertical arm member 85 relative to the support 86. The claims 87 and 88 may be used to vary the position of the arm 12 along the vertical support 86. The arm 12 includes a first horizontal arm segment 83 attached to the vertical arm segment 85 via a pivotal connection 84. A second horizontal arm segment 82 is pivotally attached to the first horizontal arm segment 83. An outermost arm segment 80 is pivotally attached to arm segment 82 via a pivotal connection 81. The connection device 81 also includes a spring-loaded tongue 85 that extends into and is connected to the arm segment 80. This tongue 85 is rotatable relative to a horizontal axis through the connection device 81 such that the arm segment 80 pivots in a vertical direction with raising and lowering of the head harness 44. In this regard, the weight compensator mechanism 54 is similar to that described above with respect to FIG. 4, except that the mechanism 54 is essentially internal to portions of the adjustable arm 12.

It should be appreciated by those skilled in the art that modifications and variations may be made to the embodiments of the invention described and illustrated herein without departing from the scope and spirit of the invention. It is intended that the invention include such modifications and variations as come within the scope and spirit of the appended claims.

What is claimed:

1. A microscope system, comprising:
    an adjustable arm attached at one end to a support mount;
    a cable suspension member configured proximal to an opposite end of said adjustable arm;
    a scope assembly connected to said suspension member so as to hang from said suspension member, said scope assembly further comprising a head harness and a microscope adjustably connected to said harness so as to be disposed continuously along an operator's line of sight so long as the operator is wearing said scope assembly; and
    an adjustable weight compensator device operably configured on said arm to compensate for weight of said scope assembly hanging on said suspension member such that the position and angular orientation of said scope assembly is slaved to movement of the operator's head simultaneously with movement of the operator's head with minimal force required by the operator to move and maintain position of said scope assembly along the operator's line of sight.

2. The microscope system as in claim 1, wherein the amount of force required by the operator to reposition said scope assembly in generally any plane of movement is less than about 2.5 lbs. of force.

3. The microscope system as in claim 2, wherein said scope assembly has a weight of less than about 8 lbs.

4. The microscope system as in claim 1, wherein said microscope is a binocular microscope.

5. The microscope system as in claim 1, wherein said adjustable arm comprises at least two arm segments pivotally connect to each other.

6. The microscope system as in claim 1, wherein said adjustable arm comprises a plurality of arm segments adjustable in at least one of a horizontal or vertical plane relative to each other, said weight compensator device operably connected between a vertically fixed arm segment and a vertically adjustable arm segment.

7. The microscope system as in claim 6, wherein said weight compensator device comprises a spring mechanism.

8. The microscope system as in claim 1, wherein said weight compensator device comprises a line tensioner mechanism configured with said suspension member.

9. The microscope system as in claim 1, wherein said scope assembly is releasably connected to said suspension member.

10. The microscope system as in claim 1, wherein said head harness comprises an adjustable strap member that encircles the operator's head, and a rigid mounting fixture configured on said strap member to which said microscope is attached so that relative movement between the operator's head and the microscope is minimized.

11. The microscope system as in claim 10, wherein said rigid mounting fixture comprises a rigid material band coincident with said strap member around at least a portion thereof, and a mounting plate attached to said rigid material band, said microscope attached to said mounting plate via a rigid connecting arm.

12. The microscope system as in claim 11, wherein said rigid connecting arm is adjustable in position relative to said mounting plate, and said microscope is adjustable in position relative to said rigid connecting arm.

13. The microscope system as in claim 12, wherein said head harness comprises an additional adjustable strap member configured to pass over the top of the operator's head.

14. The microscope system as in claim 1, wherein said support mount is one of a vertical mount, wall mount, floor mount, or ceiling mount, and said arm is adjustable in position relative to said mount.

15. The microscope system as in claim 1, wherein said weight compensator device is attached to said arm between said suspension member and said support mount.

16. The microscope system as in claim 1, further comprising at least one LED light source disposed at a periphery of said microscope to illuminate an area in front of said microscope.

17. The microscope system as in claim 16, wherein said LED light source further comprises a lens disposed to focus and direct light to said area in front of said microscope.

18. A microscope system, comprising:
    an adjustable arm attached at one end to a support mount;
    a scope assembly supported by and disposed below said adjustable arm, said scope assembly further comprising a head harness and a binocular microscope adjustably connected to said harness so as to be disposed along an operator's line of sight so long as the operator is wearing said scope assembly; and
    a weight compensator device operably configured on said adjustable arm to compensate for weight of said scope assembly supported by said adjustable arm, said weight compensator device providing a counter balancing force such that the position and angular orientation of said scope assembly is slaved to movement of the operator's head simultaneously with movement of the operator's head with a force of less than about 2.5 lbs. required by the operator to move and maintain position of said scope assembly along the operator's line of sight in generally any plane of movement.

19. The microscope system as in claim 18, wherein said scope assembly has a weight of less than about 8 lbs.

20. The microscope system as in claim 18, wherein said scope assembly is suspended from said adjustable arm by a cable suspension member.

21. The microscope system as in claim 20, wherein said weight compensator device comprises a line tensioner mechanism configured with said suspension member.

22. The microscope system as in claim 18, wherein said adjustable arm comprises a plurality of adjustable arm segments, said weight compensator device comprising a spring mechanism attached between a vertically adjustable one of said arm segments and vertically fixed one of said arm segments.

23. The microscope system as in claim 18, further comprising at least one LED light source disposed at a periphery of said microscope to illuminate an area in front of said microscope.

24. The microscope system as in claim 23, wherein said LED light source further comprises a lens disposed to focus and direct light to said area in front of said microscope.

25. A microscope system, comprising:

a scope assembly connected to one end of a cable suspension member so as to hang from said suspension member, said scope assembly further comprising a head harness and a microscope adjustably connected to said harness so as to be disposed along an operator's line of sight so long as the operator is wearing said scope assembly;

an opposite end of said cable suspension member connected to a support member; and a weight compensator device operably configured relative to said suspension member so as to compensate for weight of said scope assembly hanging on said suspension member such that the position and angular orientation of said scope assembly is slaved to movement of the operator's head simultaneously with movement of the operator's head with minimal force required by the operator to move and maintain position of said scope assembly along the operator's line of sight.

26. The microscope system as in claim 25, wherein the amount of force required by the operator to reposition said scope assembly in generally any plane of movement is less than about 2.5 lbs. of force.

27. The microscope system as in claim 25, wherein said scope assembly has a weight of less than about 8 lbs.

* * * * *